(12) United States Patent
Lindsay

(10) Patent No.: US 11,913,070 B2
(45) Date of Patent: Feb. 27, 2024

(54) METHODS FOR SEQUENCING BIOPOLYMERS

(71) Applicant: Arizona Board of Regents on behalf of Arizona State University, Scottsdale, AZ (US)

(72) Inventor: Stuart Lindsay, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 383 days.

(21) Appl. No.: 17/184,201

(22) Filed: Feb. 24, 2021

(65) Prior Publication Data
US 2021/0269869 A1 Sep. 2, 2021

Related U.S. Application Data

(60) Provisional application No. 62/983,417, filed on Feb. 28, 2020.

(51) Int. Cl.
*C12Q 1/6869* (2018.01)
*C12Q 1/00* (2006.01)
*G16B 30/20* (2019.01)
*G16B 40/10* (2019.01)
*G01N 33/487* (2006.01)
*G01N 27/12* (2006.01)

(52) U.S. Cl.
CPC ........... *C12Q 1/6869* (2013.01); *C12Q 1/005* (2013.01); *G01N 33/48721* (2013.01); *G16B 30/20* (2019.02); *G16B 40/10* (2019.02); *G01N 27/125* (2013.01)

(58) Field of Classification Search
CPC .... C12Q 1/6869; C12Q 1/005; C12Q 1/6825; C12Q 2521/10; C12Q 2565/607; C12Q 2563/116; G01N 33/48721; G01N 27/125; G01N 27/327; G16B 30/20; G16B 40/10
See application file for complete search history.

(56) References Cited

U.S. PATENT DOCUMENTS

| | | | |
|---|---|---|---|
| 5,198,543 A | 3/1993 | Blanco | |
| 6,824,974 B2 | 11/2004 | Pisharody et al. | |
| 7,632,671 B2 | 12/2009 | Tong | |
| 8,628,649 B2 | 1/2014 | Lindsay et al. | |
| 8,961,757 B2 | 2/2015 | Nuckolls et al. | |
| 8,968,540 B2 | 3/2015 | Reinhart et al. | |
| 9,140,682 B2 | 9/2015 | Lindsay et al. | |
| 9,274,430 B2 | 3/2016 | Gyarfas et al. | |
| 9,376,713 B2 | 6/2016 | Bashir et al. | |
| 9,593,372 B2 | 3/2017 | Lindsay et al. | |
| 9,938,586 B2 | 4/2018 | Liang et al. | |
| 10,379,102 B2 | 8/2019 | Lindsay et al. | |
| 10,422,787 B2 | 9/2019 | Lindsay et al. | |
| 10,508,296 B2 | 12/2019 | Merriman et al. | |
| 10,913,966 B2 | 2/2021 | Merriman et al. | |
| 2003/0124572 A1 | 7/2003 | Umek et al. | |
| 2004/0146863 A1 | 7/2004 | Pisharody et al. | |
| 2004/0249124 A1 | 12/2004 | Caruso et al. | |
| 2005/0285275 A1 | 12/2005 | Son et al. | |
| 2009/0215156 A1 | 8/2009 | Chung et al. | |
| 2009/0226899 A1 | 9/2009 | Chen | |
| 2010/0084276 A1 | 4/2010 | Lindsay | |
| 2010/0184062 A1 | 7/2010 | Steinmuller-Nethl et al. | |
| 2010/0206731 A1 | 8/2010 | Lau et al. | |
| 2010/0285514 A1 | 11/2010 | Claussen et al. | |
| 2011/0098218 A1 | 4/2011 | Han et al. | |
| 2011/0312529 A1 | 12/2011 | He et al. | |
| 2012/0228386 A1 | 9/2012 | Wu et al. | |
| 2013/0302901 A1 | 11/2013 | Lindsay et al. | |
| 2014/0141525 A1 | 5/2014 | Albert et al. | |
| 2015/0010935 A1 | 1/2015 | Lindsay et al. | |
| 2015/0017655 A1 | 1/2015 | Huang et al. | |
| 2015/0086994 A1 | 3/2015 | Williams et al. | |
| 2015/0142327 A1 | 5/2015 | Ashcroft et al. | |
| 2015/0144506 A1 | 5/2015 | Lindsay et al. | |
| 2015/0285818 A1 | 10/2015 | Banala et al. | |
| 2016/0018384 A1 | 1/2016 | Lindsay et al. | |
| 2016/0025702 A1 | 1/2016 | Lindsay et al. | |
| 2016/0083789 A1 | 3/2016 | Turner et al. | |
| 2016/0097759 A1 | 4/2016 | Lindsay et al. | |
| 2016/0108002 A1 | 4/2016 | Zhang et al. | |
| 2016/0146828 A1 | 5/2016 | Lindsay et al. | |
| 2016/0177383 A1 | 6/2016 | Ashcroft et al. | |
| 2016/0194698 A1 | 7/2016 | Lindsay | |

(Continued)

FOREIGN PATENT DOCUMENTS

CN 104359946 2/2015
EP 3976814 A1 4/2022

(Continued)

OTHER PUBLICATIONS

Yoon, Current Genomics, 10, 402-415, (Year: 2009).*
Zhang et al., ACS Nano, 14 (2), 1360-1368, (Year: Oct. 2019).*
Ackerman et al., Massively multiplexed nucleic acid detection with Cas13. Nature. Jun. 2020;582(7811):277-282.
Adhikari et al., Conductivity of individual Geobacter pili. RSC Advances, 2016. 6: p. 8354-8357.
Alloway et al., Interface Dipoles Arising from Self-Assembled Monolayers on Gold: UV-Photoemission Studies of Alkanethiols and Partially Fluorinated Alkanethiols. J. Phys. Chem. B 2003, 107:11690-11699.
Altschul et al., Basic local alignment search tool. J Mol Biol. Oct. 5, 1990;215(3):403-10.

(Continued)

*Primary Examiner* — Cynthia B Wilder
(74) *Attorney, Agent, or Firm* — Casimir Jones, S.C.; Peter J. Schlueter

(57) ABSTRACT

The present disclosure provides devices, systems, and methods related to sequencing a biopolymer. In particular, the present disclosure provides methods of obtaining a bioelectronic signature based on current fluctuations that correspond to the activity of an enzyme-of-interest. As described herein, certain aspects of the bioelectronic signature can be used to determine the sequence of a biopolymer.

20 Claims, 5 Drawing Sheets

Specification includes a Sequence Listing.

(56) References Cited

U.S. PATENT DOCUMENTS

| | | |
|---|---|---|
| 2016/0258925 A1 | 9/2016 | Gyarfas et al. |
| 2016/0280723 A1 | 9/2016 | Zhang et al. |
| 2016/0282295 A1 | 9/2016 | Wang et al. |
| 2016/0319343 A1 | 11/2016 | Korlach et al. |
| 2017/0003245 A1 | 1/2017 | Lindsay et al. |
| 2017/0016852 A1 | 1/2017 | Lindsay et al. |
| 2017/0037462 A1 | 2/2017 | Turner et al. |
| 2017/0038333 A1 | 2/2017 | Turner et al. |
| 2017/0038369 A1 | 2/2017 | Lindsay et al. |
| 2017/0044605 A1 | 2/2017 | Merriman et al. |
| 2017/0067902 A1 | 3/2017 | Zhang et al. |
| 2017/0137389 A1 | 5/2017 | Zhang et al. |
| 2017/0168039 A1 | 6/2017 | Lindsay et al. |
| 2018/0031549 A1 | 2/2018 | Chen et al. |
| 2018/0051332 A9* | 2/2018 | Esfandyarpour .... G01N 27/327 |
| 2018/0073071 A1 | 3/2018 | Ju et al. |
| 2018/0095081 A1 | 4/2018 | Albert et al. |
| 2018/0120286 A1 | 5/2018 | Lindsay et al. |
| 2018/0180567 A1 | 6/2018 | Li et al. |
| 2018/0305727 A1 | 10/2018 | Merriman et al. |
| 2018/0340220 A1 | 11/2018 | Merriman et al. |
| 2019/0094175 A1 | 3/2019 | Merriman et al. |
| 2019/0112643 A1 | 4/2019 | Aran et al. |
| 2019/0234902 A1 | 8/2019 | Lima, Jr. et al. |
| 2019/0309008 A1 | 10/2019 | Ju et al. |
| 2019/0330695 A1 | 10/2019 | Guo et al. |
| 2021/0208127 A1 | 7/2021 | Lindsay et al. |
| 2022/0098635 A1* | 3/2022 | Lindsay ................. C12Q 1/004 |

FOREIGN PATENT DOCUMENTS

| | | |
|---|---|---|
| JP | 2016188794 A | 11/2016 |
| WO | WO 2013/038272 | 3/2013 |
| WO | WO 2014/074727 | 5/2014 |
| WO | WO 2015/130781 | 9/2015 |
| WO | WO 2015/131073 | 9/2015 |
| WO | WO 2015/161119 | 10/2015 |
| WO | WO 2015/170784 A1 | 11/2015 |
| WO | WO 2016/161402 | 10/2016 |
| WO | WO 2016/210386 | 12/2016 |
| WO | WO 2017/084998 | 5/2017 |
| WO | WO 2017/123416 | 7/2017 |
| WO | WO 2017/189930 | 11/2017 |
| WO | WO 2018/026855 | 2/2018 |
| WO | WO 2018/132457 | 7/2018 |
| WO | WO 2018/200687 | 11/2018 |
| WO | WO 2019/046589 | 3/2019 |
| WO | WO 2019/086305 | 5/2019 |
| WO | WO 2019/211622 | 11/2019 |
| WO | WO 2019/217600 A1 | 11/2019 |
| WO | WO 2019/222527 | 11/2019 |
| WO | WO 2020/160300 | 8/2020 |
| WO | WO 2020/257654 | 12/2020 |
| WO | WO 2021/163275 | 8/2021 |
| WO | WO 2021/173681 | 9/2021 |
| WO | WO 2021/222791 | 11/2021 |

OTHER PUBLICATIONS

Altschul et al., Gapped BLAST and PSI-BLAST: a new generation of protein database search programs. Nucleic Acids Res. Sep. 1, 1997;25(17):3389-402.

Amdursky et al., Electronic transport via proteins. Adv Mater. Nov. 12, 2014;26(42):7142-61.

Amdursky et al., Solid-state electron transport via cytochrome c depends on electronic coupling to electrodes and across the protein. PNAS, Apr. 15, 2014, vol. 111, No. 15, pp. 5556-5561.

Artes et al., Transistor-like Behavior of Single Metalloprotein Junctions. Nano Lett.,2012, 12(6), pp. 2679-2684 (publication date (Web): Oct. 5, 2011).

Aubert et al., Intraprotein radical transfer during photoactivation of DNA photolyase. Nature. Jun. 1, 2000;405(6786):586-90.

Ausubel et al. Current Protocols in Molecular Biology, John Wiley & Sons, New York, 1998.

Bostick et al., Protein bioelectronics: a review of what we do and do not know. Rep Prog Phys. Feb. 2018;81(2):026601. 58 pages.

Chang et al., Chemical recognition and binding kinetics in a functionalized tunnel junction. Nanotechnology. Jun. 15, 2012;23(23):235101. 28 pages.

Chen, Y.-S., et al., "DNA sequencing using electrical conductance measurements of a DNA polymerase," Nature Nanotechnology, May 5, 2013, pp. 1-7; https://doi.org/10.1038/nnano.2013.71.

Chichil et al., Linkers in the structural biology of protein-protein interactions. Protein Sci. Feb. 2013;22(2):153-67.

Chin et al., Addition of p-Azido-I-phenylalanine to the Genetic Code of *Escherichia coli*. J. Am. Chem. Soc. 2002. 124,31, 9026-9027.

Choi et al. "Site-specific inhibition of integrin alpha v beta 3-vitronectin association by a serasp-val sequence through an Arg-Gly-Asp-binding site of the integrin." Proteomics, vol. 10, Issue 1, No. 1 Jan. 2010, pp. 72-80 (First published Oct. 30, 2009).

Choi et al., "Single-Molecule Lysozyme Dynamics Monitored by an Electronic Circuit," Science (2012) 335:319-324; DOI: 10.1126/science.1214824.

Cui et al., Reproducible measurement of single-molecule conductivity. Science. Oct. 19, 2001;294(5542):571-4.

Dellafiore et al., Modified Nucleoside Triphosphates for In-vitro Selection Techniques. Front Chem. May 4, 2016;4:18.

Duffy et al., Modified nucleic acids: replication, evolution, and next-generation therapeutics. BMC Biology, Sep. 2, 2020. 18:112. 14 pages.

Extended European Search Report for PCT/US2019031394, dated Jan. 5, 2022. 7 pages.

Fairhead et al., Plug-and-play pairing via defined divalent streptavidins. J Mol Biol. Jan. 9, 2014;426(1):199-214.

Fujino et al, Chimeric RNA Oligonucleotides Incorporating Triazole-Linked Trinucleotides: Synthesis and Function as mRNA in Cell-Free Translation Reactions. J Org Chem. Oct. 7, 2016;81(19):8967-8976.

Fulton et al., Purification of monoclonal antibody against Ebola GP1 protein expressed in Nicotiana benthamiana. J Chromatogr A. Apr. 10, 2015;1389:128-32.

Garg et al., Interface Electrostatics Dictates the Electron Transport via Bioelectronic Junctions. ACS Appl Mater Interfaces. Dec. 5, 2018;10(48):41599-41607.

Giese et al., Direct observation of hole transfer through DNA by hopping between adenine bases and by tunnelling. Nature. Jul. 19, 2001;412(6844):318-20.

Giese et al., Long distance charge transport through DNA: quantification and extension of the hopping model. Chemphyschem. Dec. 15, 2000;1(4):195-8.

Gonnet et al., Exhaustive matching of the entire protein sequence database. Science. Jun. 5, 1992;256(5062):1443-5.

Guo et al., Tuning electronic transport via hepta-alanine peptides junction by tryptophan doping. Proc Natl Acad Sci U S A. Sep. 27, 2016;113(39):10785-90.

Hajian et al., Detection of unamplified target genes via CRISPR-Cas9 immobilized on a graphene field-effect transistor. Nat Biomed Eng. Jun. 2019;3(6):427-437.

Harriman. Further comments on the redox potentials of tryptophan and tyrosine. Journal of Physical Chemistry 1987. 91:6102-6104.

Hohl et al. Engineering a Polyspecific Pyrrolysyl-tRNA Synthetase by a High Throughput FACS Screen. Sci Rep. Aug. 19, 2019;9(1):11971.

International Search Report and Written Opinion for PCT/US19/31394, dated Sep. 10, 2019. 11 pages.

International Search Report and Written Opinion for PCT/US20/15931, dated Jul. 27, 2020. 17 pages.

International Search Report and Written Opinion for PCT/US20/38740, dated Oct. 2, 2020. 14 pages.

International Search Report and Written Opinion for PCT/US21/17583, dated May 3, 2021. 9 pages.

International Search Report and Written Opinion for PCT/US21/19428, dated May 6, 2021. 25 pages.

International Search Report and Written Opinion for PCT/US21/27650, dated Aug. 25, 2021. 9 pages.

(56) References Cited

OTHER PUBLICATIONS

International Search Report and Written Opinion for PCT/US21/30239, dated Sep. 27, 2021. 10 pages.
International Search Report and Written Opinion for PCT/US21/34698, dated Sep. 30, 2021. 10 pages.
International Search Report and Written Opinion for PCT/US21/63851, dated Feb. 17, 2022. 9 pages.
International Search Report and Written Opinion for PCT/US21/64905, dated Mar. 17, 2022. 9 pages.
Jeffrey, An Introduction to Hydrogen Bonding. Oxford University Press New York. 1997. TOC only. 6 pages.
Kluenker et al., Monitoring Thiol-Ligand exchange on Au nanoparticle surfaces. Langmuir. Jan. 30, 2018;34(4):1700-1710.
Kotlowski Fine discrimination of volatile compounds by graphene-immobilized odorant-binding proteins, Sensors and Actuatores B: Chemical 2018 (256): 564-72.
Kyte et al., A simple method for displaying the hydropathic character of a protein. J Mol Biol. May 5, 1982;157(1):105-32.
Lagunas et al., Long distance electron transfer through the aqueous solution between redox partner proteins. Nat Commun. Dec. 4, 2018;9(1):5157.
Lai et al., Monoclonal antibody produced in plants efficiently treats West Nile virus infection in mice. Proc Natl Acad Sci U S A. Feb. 9, 2010;107(6):2419-24.
Lai et al., Robust production of virus-like particles and monoclonal antibodies with geminiviral replicon vectors in lettuce. Plant Biotechnol J. Jan. 2012;10(1):95-104.
Leary et al., Unambiguous one-molecule conductance measurements under ambient conditions. Nano Lett. Jun. 8, 2011;11(6):2236-41.
Li et al., CRISPR-SE: a brute force search engine for CRISPR design. NAR Genom Bioinform. Feb. 23, 2021;3(1):lqab013.
Li et al., Synthesis and Photovoltaic effect on electron-withdrawing units for low band gap conjugated polymers bearing bi(thienylenevinylene) side chains. Polymers. 2019, vol. 11 iss 9 pp. 1-13.
Lindsay. Ubiquitous Electron Transport in Non-Electron Transfer Proteins. Life (Basel). May 20, 2020;10(5):72. 13 pages.
Liu et al., Vertical T cellimmunodomincance and epitope entropy determine HIV-1 escape. J Clin Invest. Jan. 2013;123(1):380-93.
Main et al., Design of stable alpha-helical arrays from an idealized TPR motif. Structure. May 2003;11(5):497-508.
Malvankar et al., Tunable metallic-like conductivity in microbial nanowire networks. Nat Nanotechnol. Aug. 7, 2011;6(9):573-9.
Marakova et al., An updated evolutionary classification of CRISPR-Cas systems. Nat Rev Microbiol. Nov. 2015;13(11):722-36.
McKenzie et al., Recent progress in non-native nucleic acid modifications. Chem Soc Rev. Apr. 26, 2021;50(8):5126-5164.
Mejias et al., Controlled nanometric fibers of self-assembled designed protein scaffolds. Nanoscale. Oct. 7, 2014;6(19):10982-8.
Metsky et al., Diagnostic design with machine learning model-based optimization. bioRxiv 2020.11.28.401877: 95 pages.
Mullegama et al., Nucleic Acid Extraction from Human Biological Samples. Methods Mol Biol 2019;1897:359-383.
Nitzan. Chemical dynamics in condensed phases. Oxford University Press., Oxford. 2006. TOC only. 13 pages.
Odella et al., Controlling Proton-Coupled Electron Transfer in Bioinspired Artificial Photosynthetic Relays. J Am Chem Soc. Nov. 14, 2018;140(45):15450-15460.
Olsen et al., "Electronic Measurements of Single-Molecule Processing by DNA Polymerase I (Klenow Fragment)," Journal of the American Chemical Society (Apr. 30, 2013); pp. 1-12; DOI: 10.1021/ja311603r.
Pang et al. "Fixed-Gap Tunnel Junction for Reading DNA Nucleotides" ACS Nano, 2014, 8(12), pp. 11994-12003 (Publication Date (Web): Nov. 7, 2014).
Pearson. Using the FASTA program to search protein and DNA sequence databases. Methods Mol Biol. 1994;24:307-31.
Quast et al., Cotranslational incorporation of non-standard amino acids using cell-free protein synthesis. FEBS Lett. Jul. 8, 2015;589(15):1703-12.
Ruiz et al., Bioengineering a Single-Protein Junction. J Am Chem Soc. Nov. 1, 2017;139(43):15337-15346.
Sambrook et al., Molecular Cloning: A Laboratory Manual, 3d ed., Cold Spring Harbor Press, 2001. TOC only. 23 pages.
Sano et al., Cooperative biotin binding by streptavidin. Electrophoretic behavior and subunit association of streptavidin in the presence of 6 M urea. J Biol Chem. Feb. 25, 1990;265(6):3369-73.
Seifert, Characterization of Streptavidin Binding to Biotinylated, Binary Self-Assembled Thio Monolayers—Influence of Component Ratio and Solvent, Langmuir, 2010, 26(9): 6386-93.
Sek et al., Conductance of alpha-helical peptides trapped within molecular junctions. J Phys Chem B. Oct. 5, 2006;110(39):19671-7.
Sequences of amino acids as found on the world wide web at bmrb.wisc.edu/referenc/choufas. 4 pages.
Smith. The hydrophilic nature of a clean gold surface. J. Colloid Interface Science 1980. 75:51-55.
Staals et al., RNA targeting by the type III-A CRISPR-Cas Csm complex of Thermus thermophilus. Mol Cell. Nov. 20, 2014;56(4):518-30.
Tripkovic et al., Standard hydrogen electrode and potential of zero charge in density functional calculations. Phys. Rev. B 2011. 84:115452.
Tuchband et al., Insulated gold scanning tunneling microscopy probes for recognition tunneling in an aqueous environment. Rev Sci Instrum. Jan. 2012;83(1):015102.
Vaish et al., A novel, modification-dependent ATP-binding aptamer selected from an RNA library incorporating a cationic functionality. Biochemistry. Jul. 29, 2003;42(29):8842-51.
Vattay et al., Quantum Criticality at the Origin of Life. Journal of Physics: Conference Series 2015. 626: p. 012023. 11 pages.
Willner et al., Mediated electron transfer in glutathione reductase organized in self-assembled monolayers on Au electrodes. J. Am. Chem. Soc., 1992. 114: p. 10965-10966.
Xiao et al., Conductance titration of single-peptide molecules. J Am Chem Soc. May 5, 2004;126(17):5370-1.
Yang et al., Plant-produced Zika virus envelope protein elicits neutralizing immune responses that correlate with protective immunity against Zika virus in mice. Plant Biotechnol J. Feb. 2018;16(2):572-580.
Zhang et al., Engineering an Enzyme for Direct Electrical Monitoring of Activity. ACS Nano. Feb. 25, 2020;14(2):1360-1368.
Zhang et al., Electronic Conductance Resonance in Non-Redox-Active Proteins. J Am Chem Soc. Apr. 1, 2020;142(13):6432-6438.
Zhang et al., Electronic Decay Length in a Protein Molecule. Nano Lett. Jun. 12, 2019;19(6):4017-4022.
Zhang et al., Observation of Giant Conductance Fluctuations in a Protein. Nano Futures. 2017;1(3):035002. 25 pages.
Zhang et al., Role of contacts in long-range protein conductance. Proc Natl Acad Sci U S A. Mar. 26, 2019;116(13):5886-5891.
Zwolak et al. "Electronic Signature of DNA Nucleotides via Transverse Transport" NanoLett., 2005, 5(3), pp. 421-424 (Publication Date (Web): Feb. 12, 2005).
Anzai et al., "Avidin-biotin complexation for enzyme sensor applications" Trends in Analytical Chemistry, 1994, 13(5): 205-210.
Barhoumi et al: "Urease immobilization on biotinylated polypyrrole coated ChemFEC devices for urea biosensor development" IRBM, Apr. 1, 2008, 29(2-3): 192-201.
Cui et al: "Layer-by-layer 1 assembly of multilayer filme composed of avidin and biotin-labeled antibody for immunosensing", Biosensors And Bioelectronics, Jan. 1, 2003, 18(1): 59-67.
Hays et al., Development of capacitance based immunosensors on mixed self-assembled monolayers. Sensors and Actuators B: Chemical, Apr. 26, 2006, vol. 114, No. 2, pp. 1064-1070.
Ihalainene et al., "Application of paper-supported printed gold electrodes for impedimetric immunosensor development" Biosensors 2013, 3:1-17.
International Search Report and Written Opinion for PCT/US2022/032211, dated Sep. 29, 2022. 31 pages.

(56) References Cited

OTHER PUBLICATIONS

Maalouf R. et al., Label-Free Detection of Bacteria by Electrochemical Impedance Spectroscopy: Comparison to Surface Plasmon Resonance. Anal. Chem, May 25, 2007, vol. 79, No. 13, pp. 4879-4886.
Ouerghi et al., "Impedimetric immunosensor using avidin-biotin for antibody immobilization" Bioelectrochemistry, May 15, 2002, 56(1-2): 131-133.
Prodromids et al., "Impedimetric immunosensors—A review" Electrochimica Acta, May 30, 2010, 55(14): 4227-4233.
Shimura & Yoshida, "Heterogeneous photocatalytic hydrogen production from water and biomass derivatives" Energy Environmental Science 2011, 4: 2467.

* cited by examiner

SEQUENCE LISTING

<160> NUMBER OF SEQ ID NOS: 3

<210> SEQ ID NO 1
<211> LENGTH: 10
<212> TYPE: DNA
<213> ORGANISM: Artificial Sequence

```
<220> FEATURE:
<223> OTHER INFORMATION: Synthetic

<400> SEQUENCE: 1
aaaaaaaaaa                                                              10

<210> SEQ ID NO 2
<211> LENGTH: 15
<212> TYPE: DNA
<213> ORGANISM: Artificial Sequence
<220> FEATURE:
<223> OTHER INFORMATION: Synthetic

<400> SEQUENCE: 2
atcatcatca tcatc                                                        15

<210> SEQ ID NO 3
<211> LENGTH: 42
<212> TYPE: DNA
<213> ORGANISM: Artificial Sequence
<220> FEATURE:
<223> OTHER INFORMATION: Synthetic

<400> SEQUENCE: 3
catctactac gcttagcttg ctatcatcta tgcttagcat ga                          42
```

METHODS FOR SEQUENCING BIOPOLYMERS

RELATED APPLICATIONS

This application claims priority to and the benefit of U.S. Provisional Patent Application No. 62/983,417 filed Feb. 28, 2020, which is incorporated herein by reference in its entirety for all purposes.

GOVERNMENT SUPPORT

This invention was made with government support under Grant No. R21 HG010522 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 825 Byte ASCII (Text) file named "2021-02-24_38882-20-24_SQL_ST25.txt," created on Feb. 24, 2021.

FIELD

The present disclosure provides devices, systems, and methods related to sequencing a biopolymer. In particular, the present disclosure provides methods of obtaining a bioelectronic signature based on current fluctuations that correspond to the activity of an enzyme-of-interest. As described herein, certain aspects of the bioelectronic signature can be used to determine the sequence of a biopolymer.

BACKGROUND

As proteins perform their various functions, movements are generated that underlie these functions. The ability to develop devices, systems, and methods that measure the electrical characteristics corresponding to the fluctuations generated by an active protein can be a basis for label-free detection and analysis of protein function. For example, monitoring the functional fluctuations of an active enzyme may provide a rapid and simple method of screening candidate drug molecules that affect the enzyme's function. In other cases, the ability to monitor the fluctuations of proteins that process biopolymers (e.g., carbohydrates, polypeptides, nucleic acids, and the like) may reveal new information about their conformational changes and how those changes are linked to function. Additionally, diagnostic and analytical devices can be developed to take advantage of the electrical characteristics produced by active proteins, providing new ways to leverage biomechanical properties for practical use.

SUMMARY

Embodiments of the present disclosure include methods for sequencing a polynucleotide using a bioelectronic device. In accordance with these embodiments, the method includes introducing a template polynucleotide to the bioelectronic device; introducing a solution comprising dNTP monomers to the device comprising the template polynucleotide, each dNTP present in the solution at a pre-defined concentration; and obtaining a bioelectronic signature of polymerase activity based on current fluctuations as each complementary dNTP monomer is incorporated into the template polynucleotide. In some embodiments, at least one characteristic of the bioelectronic signature identifies each of the complementary dNTPs incorporated into to the template polynucleotide. In some embodiments, the bioelectronic device comprises a polymerase functionally coupled to at least a first electrode and a second electrode. In some embodiments, the bioelectronic device comprises a polymerase functionally coupled to both a first electrode and a second electrode.

In some embodiments, the bioelectronic signature comprises an open period corresponding to the polymerase being in an open state. In some embodiments, the duration of the open period is distinct for each dNTP monomer such that it identifies whether a particular dNTP monomer has been incorporated into the template polynucleotide.

In some embodiments, the solution comprises four dNTP monomers. In some embodiments, a first dNTP is present in the solution at a concentration such that the duration of its open period minimally overlaps with the duration of the open period of a second dNTP. In some embodiments, the second dNTP is present in the solution at a concentration such that the duration of its open period minimally overlaps with the duration of the open period of the first dNTP and a third dNTP. In some embodiments, the third dNTP is present in the solution at a concentration such that the duration of its open period minimally overlaps with the duration of the open period of the second dNTP and a fourth dNTP. In some embodiments, the fourth dNTP is present in the solution at a concentration such that the duration of its open period minimally overlaps with the duration of the open period of the third dNTP. In some embodiments, the sequence of the polynucleotide template can be accurately determined from the duration of each open period. In some embodiments, the sequence of the polynucleotide can be accurately determined from the duration of each open period and/or one or more characteristics of the closed period.

In some embodiments, the duration of open periods for each dNTP are determined based on a distribution of a plurality of open duration periods. In some embodiments, the first dNTP is present at a saturating concentration. In some embodiments, extent of overlap is 1% or less.

In some embodiments, the bioelectronic signature comprises a closed period corresponding to the polymerase being in a closed state. In some embodiments, at least one characteristic of the closed period varies based on the previously incorporated nucleotide. In some embodiments, at least one characteristic of the closed period is identified using a method comprising machine learning. In some embodiments, the machine learning method comprises Hidden-Markov Modeling or Bayesean non-parametric analysis.

In some embodiments, a combination of at least one characteristic of the closed period and at least one characteristic of the open period is used to identify each of the complementary dNTPs incorporated into to the template polynucleotide.

In some embodiments, the polynucleotide template is DNA. In some embodiments, the polynucleotide template is RNA. In some embodiments, the dNTP monomers comprise adenine (dATP), cytosine (dCTP), guanine (dGTP), thymine (dTTP), and/or uridine (dUTP), including any derivatives or variants thereof.

In some embodiments, the exonuclease activity of the polymerase is disabled. In some embodiments, the polymerase is functionally coupled to the first and second electrodes using a linker comprising thio-streptavidin. In some embodiments, linker is attached to a region of the polymerase that is inactive.

In some embodiments, the method comprises applying a voltage bias between the first and second electrodes that is 100 mV or less.

Embodiments of the present disclosure also include a method of calibrating a bioelectronic device. In accordance with these embodiments, the method includes introducing a template polynucleotide to the bioelectronic device; introducing a solution comprising dNTP monomers to the device comprising the template polynucleotide, each dNTP present in the solution at a saturating concentration; obtaining a bioelectronic signature of polymerase activity based on current fluctuations as each complementary dNTP monomer is incorporated into the template polynucleotide, wherein the bioelectronic signature comprises an open period corresponding to the polymerase being in an open state; and measuring or determining the intrinsic distribution of the open periods for each dNTP.

In some embodiments, the bioelectronic device is calibrated based on the distribution of open periods. In some embodiments, the bioelectronic device comprises a polymerase functionally coupled to at least a first electrode and a second electrode. In some embodiments, the bioelectronic device comprises a polymerase functionally coupled to both a first electrode and a second electrode.

In some embodiments, the bioelectronic signature comprises a closed period corresponding to the polymerase being in a closed state, and the bioelectronic device is calibrated based on at least one characteristic of the closed period.

DETAILED DESCRIPTION

Figure 1:
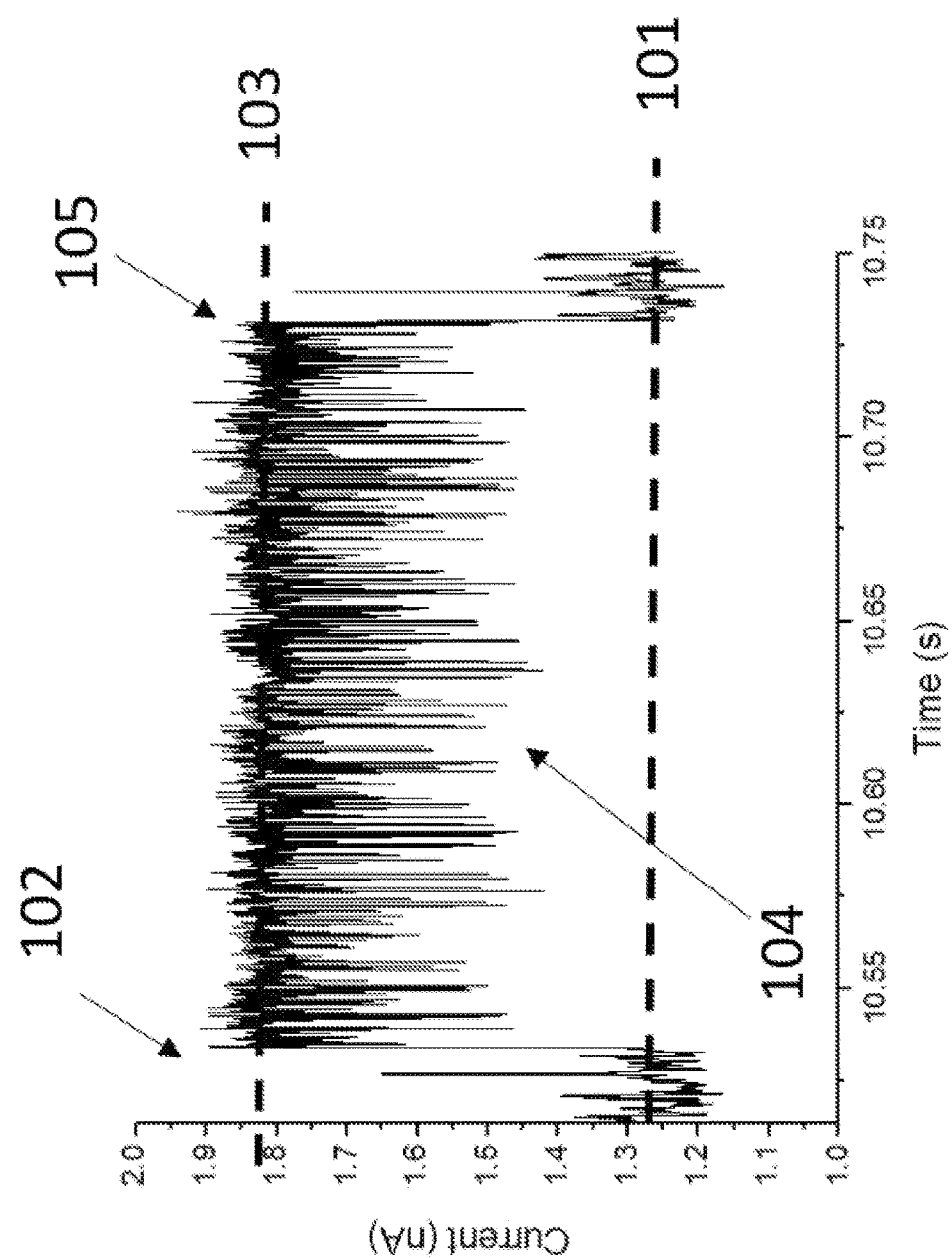
FIG. 1: Representative graph showing a bioelectronic signature of enzyme activity based on current fluctuations, according to one embodiment of the present disclosure.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

As noted herein, the disclosed embodiments have been presented for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, compositions, systems and apparatuses/devices which may further include any and all elements from any other disclosed methods, compositions, systems, and devices, including any and all elements corresponding to detecting protein activity. In other words, elements from one or another disclosed embodiments may be interchangeable with elements from other disclosed embodiments. Moreover, some further embodiments may be realized by combining one and/or another feature disclosed herein with methods, compositions, systems and devices, and one or more features thereof, disclosed in materials incorporated by reference. In addition, one or more features/elements of disclosed embodiments may be removed and still result in patentable subject matter (and thus, resulting in yet more embodiments of the subject disclosure). Furthermore, some embodiments correspond to methods, compositions, systems, and devices which specifically lack one and/or another element, structure, and/or steps (as applicable), as compared to teachings of the prior art, and therefore represent patentable subject matter and are distinguishable therefrom (i.e. claims directed to such embodiments may contain negative limitations to note the lack of one or more features prior art teachings).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

2. Bioelectronic Devices and Systems

Embodiments of the present disclosure include devices, systems, and methods related to sequencing a biopolymer. In particular, the present disclosure provides methods of obtaining a bioelectronic signature based on current fluctuations that corresponds to the activity of an enzyme-of-interest. As described further herein, certain aspects of the bioelectronic signature of the enzyme-of-interest can be used to determine the sequence of a biopolymer.

In accordance with these embodiments, the enzyme-of-interest can be a polymerase, and various aspects of a bioelectronic signature of a polymerase as it adds nucleotide monomers to a template polynucleotide strand can be used to determine the sequence of that template polynucleotide. For example, the bioelectronic signature of polymerase activity can be based on current fluctuations as each complementary nucleotide monomer is incorporated into the template polynucleotide; and the signature can be obtained using a bioelectronic device comprising a polymerase functionally coupled to at least a first electrode and a second electrode. In some embodiments, the bioelectronic device comprises a polymerase functionally coupled to both a first electrode and a second electrode. The term "nucleotide" generally refers to a base-sugar-phosphate combination and includes ribonucleoside triphosphates ATP, UTP, CTG, GTP and deoxyribonucleoside triphosphates such as dATP, dCTP, dITP, dUTP, dGTP, dTTP, or derivatives thereof.

In some embodiments, the conductance of a polymerase molecule doubles when the molecule makes a transition from the open state (poised and ready to accept an incoming dNTP monomer) and the closed state (incorporating the incoming dNTP and translating the new double helix within the polymerase). A representative illustration of a typical electrical signal obtained during this process in shown in FIG. 1. In the inactive state, the current through the polymerase is at a low baseline level (101). Once dNTPs are added, the current jumps to the new higher conductance (102) associated with the closed state (103). After each new nucleotide is incorporated, the current dips down (104), which indicates a transition to the next open state. In the trace shown in FIG. 1, the downward sweep in current is limited by the response time of the electronics. That is, slower openings do come down all the way to the background level of current (101). In this particular example dataset, the polymerase has not captured a new template (105), and the current drops back to the baseline level (101).

Figure 2:
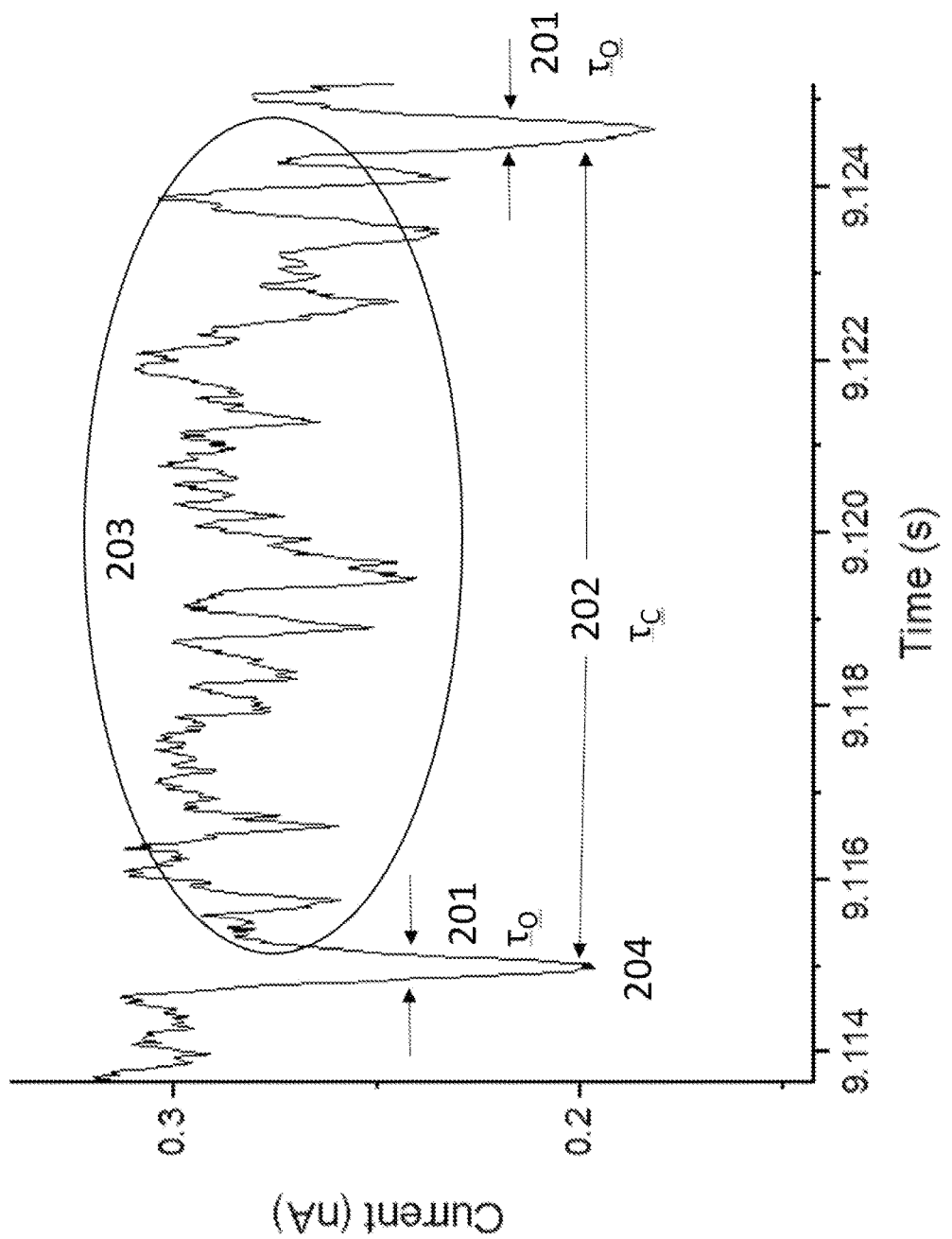
FIG. 2: Representative graph of an expanded portion of the bioelectronic signature of FIG. 1, which includes the portion of time during which a new monomer (e.g., dNTP) is incorporated into a biopolymer as the enzyme transitions from an open state (201) to a closed state (202), according to one embodiment of the present disclosure.

The bioelectronic signatures of polymerase activity contain information both in the transient open states and in the closed regions in between. For example, FIG. 2 includes an expanded portion of the bioelectronic signature of FIG. 1, which includes the portion of time during which a new monomer (e.g., dNTP) is incorporated into a biopolymer as the enzyme transitions from an open state (201) to a closed state (202). The two transient openings (201) in FIG. 2 demarcate the time for the reaction of cleaving the triphosphate, incorporating the new nucleotide, and translating the DNA, shown as $\tau_C$ (the closed interval, or 202). The width of the open state is shown between arrows as $\tau_O$. The current (203) in between the first opening (204) and the subsequent reopening contains features or characteristics (203) that reflect the incorporation of the nucleotide captured in the first opening (204).

As described further herein, the various features or characteristics of the bioelectronic signature of an active polymerase can be used to determine the sequence of a polynucleotide template. Additionally, as would be recognized by one of skill in the art based on the present disclosure, the methods of obtaining a bioelectronic signature and extracting various characteristics described herein can be used to determine the sequence of any biopolymer and any corresponding enzyme-of-interest, including but not limited to polymerase, a nuclease, a proteasome, a glycopeptidase, a glycosidase, a kinase and an endonuclease.

Figure 3:
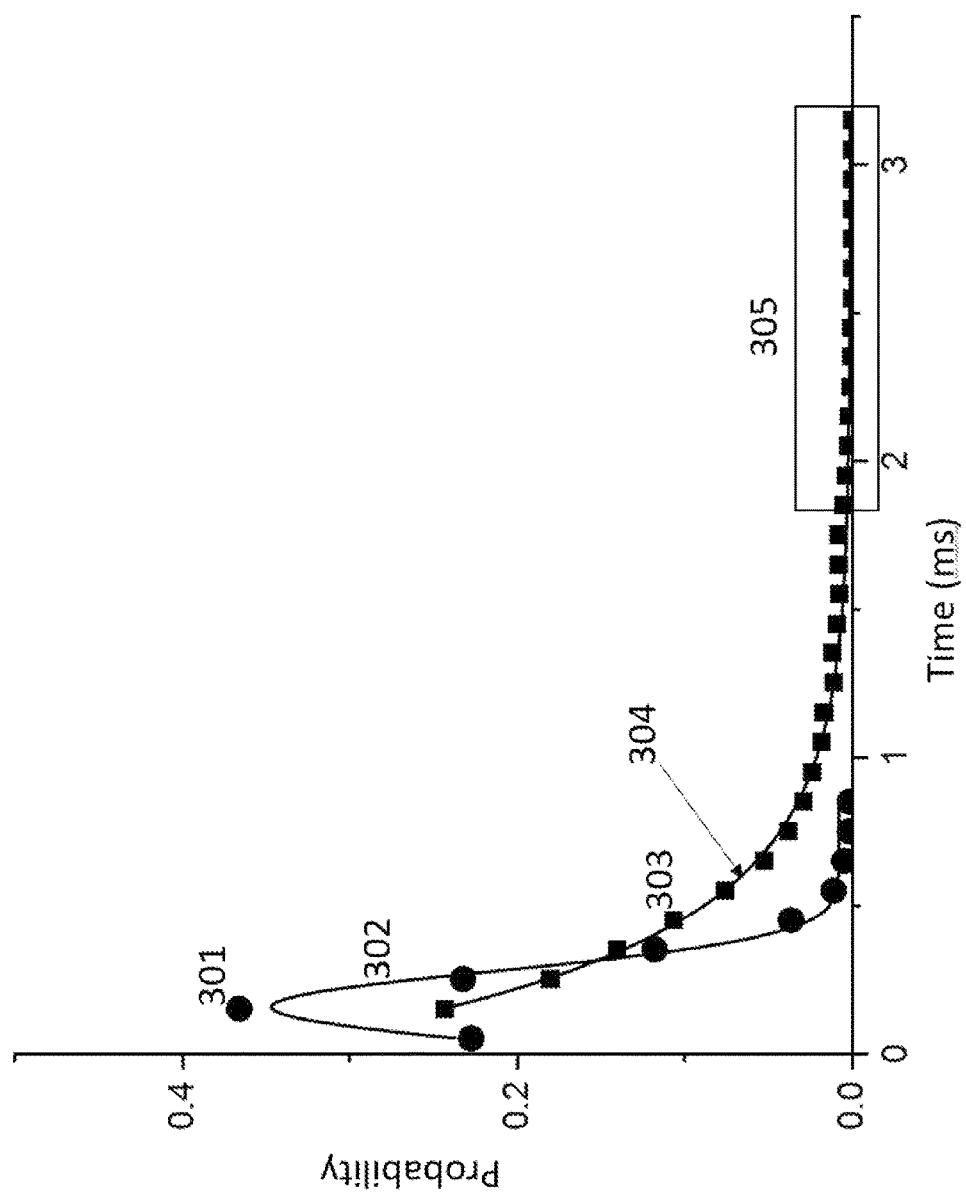
FIG. 3: Representative graph of distribution times for which an enzyme-of-interest (e.g., polymerase) resides in an open state or conformation, awaiting arrival of a monomer (e.g., dNTP), according to one embodiment of the present disclosure.

As further provided in FIG. 3, the selection of a complementary dNTP occurs during the open state (201), and the distribution of values of $\tau_O$ is sensitive to the composition of the dNTP solution (e.g., concentration). FIG. 3 shows measured probabilities of a given value of to for (301—dots) a homopolymer template consisting of 10 A bases in a 1 mM solution of the complementary dNTP, i.e., dTTP. The fitted distribution curve (302) is a sharp Gaussian with a peak at 0.16 ms and a width of 0.3 ms.

In contrast, when the polymerase has to search for the complementary dNTP, the distribution of open times is much broader, as shown by the squares (303). In this example, the template comprised a five-fold repeat of the sequence ATC in a mM solution of all four dNTPs. Now the distribution is fitted by an exponential (304), with open times that are as long as 3 ms (though less than 1% of all values exceed about 2 ms, as marked by the box 305).

These times reflect the intrinsic response of the polymerase, as can be seen by considering the time between incoming dNTPs at these mM concentrations.

The flux, I, of molecules into s sphere of radius $R_p$ (by which is meant the radius of the polymerase, ~3 nm) for a molecule diffusion constant D and a concentration [C] particles/m$^3$ is $$I = 4\pi R_p D[C]$$

The diffusion constant of the dNTPs is given by the Einstein-Smoluchowski relation and Stoke's law as $$D = \frac{kT}{6\pi\eta R_N}$$

Here, $R_N$ is the radius of a dNTP and $\eta$ is the viscosity of water ($10^{-3}$ Pa·s at 300K).

Accordingly $$I = \frac{2}{3}\frac{kT}{\eta}\left(\frac{R_p}{R_N}\right)[C]$$

where I is the number of particles entering the polymerase per second for a concentration in the bulk of [C] is in particles/m$^3$. This can be expressed in terms of the Molarity (M) times 1000×$N_A$ ($N_A$ is Avogadro's Number) giving $$I = \frac{2}{3}\frac{kT}{\eta}\left(\frac{R_p}{R_N}\right)[M] \times 6 \times 10^{26}$$

At 300K, kT=4.14×10$^{-21}$ J, and $\eta$ for water is $10^{-3}$ Pa·s, so $$I \approx 3\left(\frac{R_p}{R_N}\right)[M] \times 6 \times 10^8 = 1.8\left(\frac{R_p}{R_N}\right)[M] \times 10^9 \text{ per second} \quad (1)$$

With $R_p/R_n$~3 this give a flux of about 5×10$^6$ at 1 mM dNTP (or a time between arrivals of about 0.2 µs). Thus, dNTPs are arriving at the polymerase at the rate of more than 100 per fastest opening event. T times shown in FIG. 3, therefore, represent the intrinsic response time of the polymerase. In the case where the correct dNTP is always present (301), this is consistently about 0.16 ms. When the polymerase has to stay open to find the correct complementary nucleotide among the four possible dNTPs, the distribution of times is much broader (303). Nearly all search events are over by about 3 ms at mM concentration of dNTPs.

Equation 1 can be used to predict the arrival rate of dNTPs at a reduced concentration. Importantly, this arrival rate will be distributed according to a Poisson distribution:

$$\exp\left(-\frac{(t-\mu)^2}{2\mu}\right)$$

which has the special property that the mean interval between arrivals, µ is also the variance of the distribution.

Figure 4:
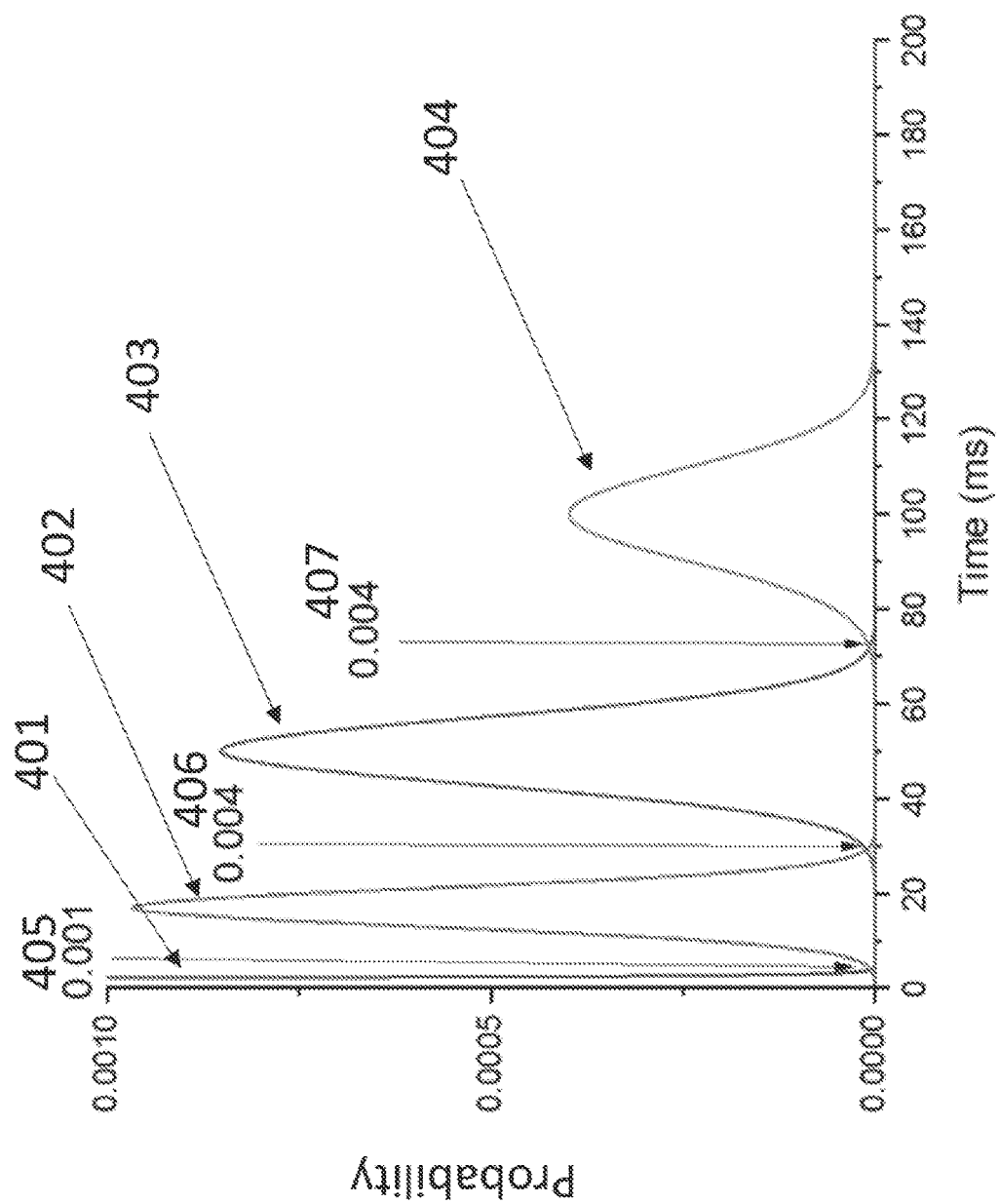
FIG. 4: Representative graph of distribution times for which an enzyme-of-interest (e.g., polymerase) resides in an open state or conformation, awaiting arrival of a monomer (e.g., dNTP), with each monomer present in a solution at pre-defined concentrations, according to one embodiment of the present disclosure.

FIG. 4 shows the intrinsic distribution of open times for the polymerase at mM dNTP's as the exponential close to the origin (401). The adjacent distribution (402) is calculated using equation 2 with µ=17 ms. Equation 1 gives $$[M] = \frac{I}{54} \text{nM}$$

As shown in this exemplary data, a 17 ms interval corresponds to 1=58.8 or an 11 nM solution to give the distribution of arrival times shown by (402). In this case, the interval between arrivals is much longer than the intrinsic response of the polymerase, so this dominates the open state lifetime. Thus, if a first dNTP is present at mM concentration, and a second dNTP at 11 nM, the overlap of the open time distributions will be given by the overlap between curves 401 and 402 (these curves are all normalized so that the total probability=1). This overlap (405) is about 0.001 or about one tenth of a percent. A further dilution of a third dNTP to 3.8 nM would result in µ=50 ms, giving the curve labeled 403. A dilution of a fourth dNTP to 1.9 nM gives µ=100 ms, with the resulting distribution plotted as the curve labeled as 404. For the dNTP represented by the curve 403, the overlap with curve 402 is 0.004 (406) and with curve 404 also 0.004 (407). Thus, the nucleotide being incorporated following an opening event can be identified by the duration of the open event to better than 1%.

In some embodiments, a first dNTP can be present in a solution at a concentration ranging from about 1 mM to about 10 mM, from about 1 mM to about 8 mM, from about 1 mM to about 6 mM, from about 1 mM to about 5 mM, from about 1 mM to about 4 mM, from about 1 mM to about 3 mM, or from about 1 mM to about 2 mM. In some embodiments, the first dNTP can be present in a solution at a concentration ranging from about 2 mM to about 10 mM, from about 4 mM to about 10 mM, from about 5, mM to about 10 mM, from about 6 mM to about 10 mM, from about 7 mM to about 10 mM, from about 8 mM to about 10 mM, or from about 8 mM to about 10 mM. In some embodiments, the first dNTP can be present in the solution at a concentration of about 1 mM, 2 mM, 3 mM, 4 mM, 5 mM, 6 mM, 7 mM, 8 mM, 9 mM, or 10 mM. Accordingly, in some embodiments, the second dNTP can be present in a solution at a concentration ranging from about 5 nM to about 15 nM, from about 10 nM to about 15 nM, from about 12 nM to about 15 nM, from about 5 nM to about 12 nM, from about 5 nM to about 10 nM, from about 5 nM to about 8 nM, from about 7 nM to about 12 nM, or from about 8 nM to about 10 nM. In some embodiments, the second dNTP can be present in the solution at a concentration of about 5 nM, 6 nM, 7 nM, 8 nM, 9 nM, 10 nM, 11 nM, 12 nM, 13 nM, 14 nM, or 15 nM. Accordingly, in some embodiments, the third dNTP can be present in a solution at a concentrating ranging from about 1 nM to about 10 nM, from about 1 nM to about 8 nM, from about 1 nM to about 6 nM, from about 1 nM to about 5 nM, from about 2 nM to about 10 nM, from about 3 nM to about 10 nM, from about 2 nM to about 8 nM, or from about 2 nM to about 6 nM. In some embodiments, the third dNTP can be present in the solution at a concentration of about 1 nM, 2 nM, 3 nM, 4 nM, 5 nM, 6 nM, 7 nM, 8 nM, 9 nM, or 10 nM. Accordingly, in some embodiments, the fourth dNTP can be present in a solution at a concentrating ranging from about 0.1 nM to about 5 nM, from about 0.1 nM to about 2.5 nM, from about 0.1 nM to about 1 nM, from about 0.5 nM to about 5 nM, from about 0.5 nM to about 2.5 nM, from about 1 nM to about 5 nM, from about 1 nM to about 4 nM, or from about 1 nM to about 2.5 nM. In some embodiments, the fourth dNTP can be present in the solution at a concentration of about 1.5 nM, 1.6 nM, 1.7 nM, 1.8 nM, 1.9 nM, 2 nM, 2.1 nM, 2.2 nM, 2.3 nM, 2.4 nM or 2.5 nM. As would be recognized by one of ordinary skill in the art based on the present disclosure, these concentrations of dNTPs are not meant to be limiting, and can be adjusted based on various aspects of the methods described herein (e.g., template sequence and structure).

As shown in Tables 1 and 2 (below), the distribution of open and closed times varies with sequence and template structure. These data show the measured distributions of times for the following sequences: (1) AAAAAAAAAA (SEQ ID NO: 1)—single stranded oligomer (A10), dTTP only in the polymerization buffer; (2) ATCATCATCAT-CATC (SEQ ID NO: 2)—single stranded oligomer (ATC5), all 4 dNTPs present; and (3) catctactacgcttagcttgctatcatc-tatgcttagcatga (SEQ ID NO: 3)—circular template, all 4 dNTPs present.

TABLE 1

Open state times for three template sequences.

| Sequence | Open state 1 | Fraction state 1 | Open State 2 | Fraction state 2 |
|---|---|---|---|---|
| A10 | 0.26 ms | 1.00 | | |
| ATC5 | 0.22 ms | 0.76 | 1.47 ms | 0.24 |
| 42 nt circle | 0.12 ms | 0.85 | 0.78 ms | 0.15 |

TABLE 2

Closed state times for three template sequences.

| Sequence | Closed state 1 | Fraction state 1 | Closed State 2 | Fraction state 2 |
|---|---|---|---|---|
| A10 | 0.37 ms | 1.00 | | |
| ATC5 | 0.35 ms | 0.71 | 2.7 ms | 0.29 |
| 42 nt circle | 0.12 ms | 0.56 | 1.96 ms | 0.44 |

The homopolymer A10 is characterized by just one open state and one closed state. The heteropolymer ATC5 is characterized by 2 open times, one as fast as that for A10 being about ¾ of the events with ¼ being much slower (Table 1). Likewise, the majority (about ¾) of its closed states are of as short a duration as for the homopolymer, with the remaining ¼ being much slower (Table 2). The circular template, with a heteropolymer sequence, also manifests two states in both its open and closed states, but both events are faster than the events in the linear polymers.

Taken together, these data show that the open times are sensitive to the nucleotide composition of the buffer. In the case of A10, where only dTTPs are present, there is just one (fast) open time. When all four nucleotides are present, there are two open states. The short open state likely corresponds to capture of the correct nucleotide at first try, while the longer open times likely correspond to capture, followed by rejection of a non-complementary nucleotide. The data also show how the closed times (corresponding to the catalytic part of the cycle) also depend on sequence. For the homopolymer A10, there is only one fast closed time. The heteropolymers both have two distinct closed times, one fast and the second almost ten times longer, which illustrates how some of the nucleotide incorporations take longer.

Figure 5:
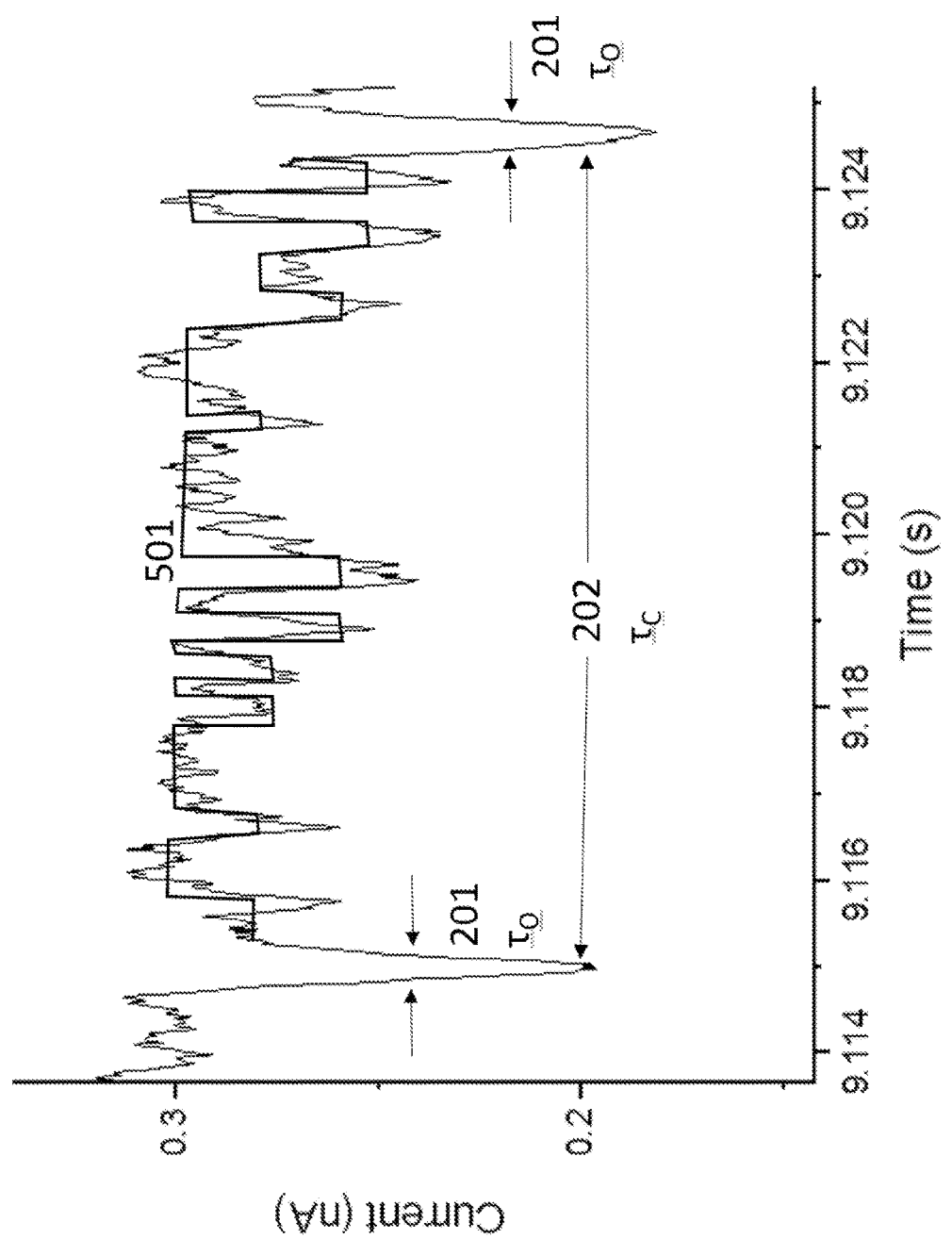
FIG. 5: Representative graph of an expanded portion of the bioelectronic signature of FIG. 1, which includes the portion of time during which a new monomer (e.g., dNTP) is incorporated into a biopolymer as the enzyme transitions from an open state (201) to a closed state (202); certain characteristics of the bioelectronic signature can be extracted (e.g., current fluctuations in the closed state) using Hidden Markov Modeling and/or Baysian Nonparametric Modeling, which can form a basis for determining the sequence of a biopolymer.

Referring to the data represented in FIG. 5, the ability to associate a given closed event (202) with the incorporation of a particular nucleotide allows for further identification of signal features or characteristics associated with a particular nucleotide. Additionally, the incorporation of a particular nucleotide on top of a particular previously incorporated nucleotide also allows for further identification of signal features or characteristics associated with a particular nucleotide, such that signal features in the closed interval reflect 16 such combinations ("base stacking"). While the open states represent large changes in current relative to the closed states, the changes of current in the closed state are stochastic and subject to noise. However, the underlying levels can be extracted in a model-independent manner using, for example, the infinite Hidden Markov model together with Bayesian nonparametric methods. In consequence, characteristic levels can be located in a model-free manner, as shown by the "hidden" underlying states (501) in FIG. 5.

In accordance with the embodiments described herein, the present disclosure provides methods for sequencing a polynucleotide using a bioelectronic device. In some embodiments, the method includes introducing a template polynucleotide to the bioelectronic device, and introducing a solution comprising dNTP monomers to the device comprising the template polynucleotide. In some embodiments, each dNTP is present in the solution at a pre-defined concentration. In some embodiments, the method includes obtaining a bioelectronic signature of polymerase activity based on current fluctuations as each complementary dNTP monomer is incorporated into the template polynucleotide. In some embodiments, at least one characteristic of the bioelectronic signature identifies each of the complementary dNTPs incorporated into to the template polynucleotide. In some embodiments, the bioelectronic device comprises a polymerase functionally coupled to at least first electrode and a second electrode. In some embodiments, the bioelectronic device comprises a polymerase functionally coupled to both a first electrode and a second electrode.

In some embodiments, the bioelectronic signature comprises an open period corresponding to the polymerase being in an open state. In some embodiments, the duration of the open period is distinct for each dNTP monomer such that it identifies whether a particular dNTP monomer has been incorporated into the template polynucleotide. In some embodiments, the solution comprises four dNTP monomers. In some embodiments, a first dNTP is present in the solution at a concentration such that the duration of its open period minimally overlaps with the duration of the open period of a second dNTP. In some embodiments, a second dNTP is present in the solution at a concentration such that the duration of its open period minimally overlaps with the duration of the open period of the first dNTP and a third dNTP. In some embodiments, the third dNTP is present in the solution at a concentration such that the duration of its open period minimally overlaps with the duration of the open period of the second dNTP and a fourth dNTP. In some embodiments, the fourth dNTP is present in the solution at a concentration such that the duration of its open period minimally overlaps with the duration of the open period of the third dNTP. In accordance with these embodiments, the sequence of the polynucleotide template can be accurately determined from the duration of each open period. In some embodiments, the sequence of the polynucleotide can be accurately determined from the duration of each open period and/or one or more characteristics of the closed period.

In some embodiments, the duration of open periods for each dNTP are determined based on a distribution of a plurality of open duration periods. In some embodiments, the first dNTP is present at a saturating concentration. In some embodiments, extent of overlap is 1% or less. In some embodiments, the extent to which the distributions minimally overlap is 1% or less. In some embodiments, the extent to which the distributions minimally overlap is 0.9% or less. In some embodiments, the extent to which the distributions minimally overlap is 0.8% or less. In some embodiments, the extent to which the distributions minimally overlap is 0.7% or less. In some embodiments, the extent to which the distributions minimally overlap is 0.6% or less. In some embodiments, the extent to which the distributions minimally overlap is 0.5% or less. In some embodiments, the extent to which the distributions minimally overlap is 0.4% or less. In some embodiments, the extent to which the distributions minimally overlap is 0.3% or less. In some embodiments, the extent to which the distributions minimally overlap is 0.2% or less. In some embodiments, the extent to which the distributions minimally overlap is 0.1% or less. In some embodiments, the extent to which the distributions minimally overlap is 0.075% or less. In some embodiments, the extent to which the distributions minimally overlap is 0.050% or less. In some embodiments, the extent to which the distributions minimally overlap is 0.025% or less. In some embodiments, the extent to which the distributions minimally overlap is 0.010% or less. In some embodiments, the extent to which the distributions minimally overlap is 0.005% or less. In some embodiments, the extent to which the distributions minimally overlap is 0.001% or less. In some embodiments, the extent to which the distributions minimally overlap is 0.0001% or less.

In some embodiments, the bioelectronic signature comprises a closed period corresponding to the polymerase being in a closed state. In some embodiments, at least one characteristic of the closed period varies based on the previously incorporated nucleotide. In some embodiments, at least one characteristic of the closed period is identified using a method comprising machine learning. In some embodiments, the machine learning method comprises Hidden-Markov Modeling or Bayesean non-parametric analysis. In some embodiments, a combination of at least one characteristic of the closed period and at least one characteristic of the open period is used to identify each of the complementary dNTPs incorporated into to the template polynucleotide. In some embodiments, the polynucleotide template is DNA. In some embodiments, the polynucleotide template is RNA. In some embodiments, the dNTP monomers comprise adenine (dATP), cytosine (dCTP), guanine (dGTP), thymine (dTTP), and/or uridine (dUTP), including any derivatives or variants thereof.

As persons of ordinary skill in the art will readily recognize and appreciate after having benefited from the teachings of the present disclosure, the methods described herein can be used with any bioelectronic device that senses the duration of the open and closed states of an enzyme (e.g., polymerase). Exemplary devices include, but are not limited to, the bioelectronic devices and systems disclosed in U.S. Pat. No. 10,422,787 and PCT Appln. No. PCT/US2019/032707, both of which are herein incorporated by reference in their entirety and for all purposes. Additionally, it will be readily recognized and appreciated by those of ordinary skill in the art based on the present disclosure that the forgoing embodiments apply equally to (and include) sequencing RNAs with the substitution of rNTPs for dNTPs and the use of an RNA polymerase.

In accordance with these embodiments, the polymerase can be functionally coupled to the first and second electrodes using a linker comprising thio-streptavidin. In some embodiments, the polymerase is biotinylated. In some embodiments, the linker is attached to a region of the polymerase that is inactive. In some embodiments, the polymerase and the first and second electrodes are biotinylated, and the linker comprises a streptavidin molecule comprising at least two biotin binding sites. In some embodiments, the exonuclease activity of the polymerase is disabled. In some embodiments, the gap has a width of about 1.0 nm to about 20.0 nm. In some embodiments, the first and second electrodes are separated by a dielectric layer. In some embodiments, the method comprises applying a voltage bias between the first and second electrodes that is 100 mV or less.

Embodiments of the present disclosure also include a system for direct electrical measurement of polymerase activity. In accordance with these embodiments, the system includes any of the bioelectronic devices described herein, a means for introducing dNTPs capable of interacting with the polymerase, a means for applying a voltage bias between the first and second electrodes that is 100 mV or less, and a means for monitoring fluctuations that occur as the dNTPs are incorporated into a template polynucleotide by the polymerase.

Embodiments of the present disclosure also include a method of calibrating a bioelectronic device. In accordance with these embodiments, the method includes introducing a template polynucleotide to the bioelectronic device; introducing a solution comprising dNTP monomers to the device comprising the template polynucleotide, each dNTP present in the solution at a saturating concentration; obtaining a bioelectronic signature of polymerase activity based on current fluctuations as each complementary dNTP monomer is incorporated into the template polynucleotide, wherein the bioelectronic signature comprises an open period corresponding to the polymerase being in an open state; and measuring or determining the intrinsic distribution of the open periods for each dNTP.

In some embodiments, the bioelectronic device is calibrated based on the distribution of open periods. In some embodiments, the bioelectronic device comprises a polymerase functionally coupled to at least a first electrode and a second electrode. In some embodiments, the bioelectronic device comprises a polymerase functionally coupled to both a first electrode and a second electrode. In some embodiments, the bioelectronic signature comprises a closed period corresponding to the polymerase being in a closed state, and the bioelectronic device is calibrated based on at least one characteristic of the closed period.

Embodiments of the present disclosure also include methods of calling bases in electrical signals from a polymerase protein spanning a junction. These methods include measuring the intrinsic distribution of opening times for a polymerase functioning in a saturating concentration of dNTPs; repeating the measurement in a solution in which at least one dNTP is diluted such that its incorporation can be identified by corresponding increased time of the open state; characterizing signal features of both the open state and the following closed state in terms of the nucleotide being incorporated and the previously incorporated nucleotide, wherein the nucleotide is first identified using the dilution method described herein; and optimizing the dilutions of each nucleotide and the use of signals parameters so that the desired sequencing accuracy is obtained at the fastest read rate.

In some embodiments, the methods provided herein include measuring or determining the opening state of a polymerase by introducing a first solution comprising a DNA template to a device, wherein the device comprises a first and a second electrode separated by a gap, and a polymerase attached to the first and second electrodes; introducing a second solution comprising four dNTPs to the product of step the previous step under conditions that allow for incorporation of the dNTP complementary to the DNA template, wherein the dNTPs are present in the solution at saturating concentrations; and measuring the intrinsic distribution of opening times for the polymerase.

In some embodiments, the methods of the present disclosure include calibrating a sequencing device comprising a first and a second electrode separated by a gap and a polymerase attached to the first and the second electrode. In accordance with these embodiments, the method includes introducing a first solution comprising a DNA template to a device, wherein the device comprises a first and a second electrode separated by a gap, and a polymerase attached to the first and second electrodes; introducing a second solution comprising four dNTPs to the product of the previous step under conditions that allow for incorporation of the dNTP complementary to the DNA template, wherein the dNTPs are present in the solution at saturating concentrations; and measuring the intrinsic distribution of opening times for the polymerase, wherein the sequencing device is calibrated from the measured intrinsic distribution of opening times.

In some embodiments, the methods of the present disclosure include identifying a base incorporated into a strand of DNA. In accordance with these embodiments, the method includes introducing a first solution comprising a DNA template to a device, wherein the device comprises a first and a second electrode separated by a gap, and a polymerase attached to the first and second electrodes, and wherein the device has been calibrated according to the method described above; introducing a second solution comprising four dNTPs to the product of the previous step under conditions that allow for incorporation of the dNTP complementary to the DNA template, wherein the first dNTP is present in the solution at a concentration such that its distribution of arrival times minimally overlaps with the distribution of polymerase opening times in a saturated concentration of the second dNTP, the second dNTP is present in the solution at a concentration such that its distribution of arrival times minimally overlaps with the distribution of arrival times of the first dNTP, the third dNTP is present in the solution at a concentration such that its distribution of arrival time minimally overlaps with the distribution of arrival times of the second dNTP and the fourth dNTP is present in the solution at a concentration such that its distribution of arrival times minimally overlaps with the distribution of arrival times of the third dNTP; and measuring current over time; wherein the base is identified from (or based on) the known distribution opening time of the polymerase in a given set of concentrations of nucleotides.

In some embodiments, the methods of the present disclosure include sequencing DNA. In accordance with these embodiments, the method includes introducing a first solution comprising a DNA template to a device, wherein the device comprises a first and a second electrode separated by a gap, and a polymerase attached to the first and second electrodes, and wherein the device has been calibrated according to the method described above; introducing a second solution comprising four dNTPs to the product of the previous step under conditions that allow for incorporation of the dNTP complementary to the DNA template, wherein the first dNTP is present at a saturating concentration in the solution, the second dNTP is present in the solution at a concentration such that its distribution of arrival times overlaps minimally with the distribution of arrival times of the first dNTP, the third dNTP is present in the solution at a concentration such that its distribution of arrival times overlaps minimally with the distribution of arrival times of the second dNTP and the fourth dNTP is present in the solution at a concentration such that its distribution of arrival time overlaps minimally with the distribution of arrival times of the third dNTP; and measuring current over time; wherein the DNA is sequenced from (or based on) the known distribution opening times of the polymerase in the given concentrations of first, second, third and fourth dNTPs.

In some embodiments, the methods of the present disclosure include improving the accuracy of biopolymer sequencing systems and methods (e.g., DNA sequencing, RNA sequencing, or other biopolymer sequencing). In accordance with these embodiments, the method includes collecting recordings of current over time according to the methods described above, and collecting the portions of the current signal from the closed state in between the open state signals and sorting them in terms of the nucleotide incorporated at a given opening event, and the nucleotide incorporated in the prior event to yield a collection of a plurality of sets (e.g., 16 sets) of closed states signals, each one of which is associated with incorporation of a given pair of nucleotides in two sequential incorporation events. In some embodiments, the method includes applying one or more machine learning methods to locate signal features in the closed-state current associated with a given pair of nucleotides in two sequential incorporation events. In some embodiments, machine-learning methods may include Hidden-Markov Modeling or Bayesean non-parametric analysis, for example.

What is claimed is:

1. A method for sequencing a polynucleotide using a bioelectronic device, the method comprising:
    (a) introducing a template polynucleotide to the bioelectronic device, wherein the bioelectronic device comprises a polymerase functionally coupled to at least one of a first electrode and a second electrode;
    (b) introducing a solution comprising dNTP monomers to the device comprising the template polynucleotide, each dNTP present in the solution at a pre-defined concentration; and
    (c) obtaining a bioelectronic signature of polymerase activity based on current fluctuations as each complementary dNTP monomer is incorporated into the template polynucleotide;
    wherein at least one characteristic of the bioelectronic signature identifies each of the complementary dNTPs incorporated into to the template polynucleotide.

2. The method of claim 1, wherein the bioelectronic signature comprises an open period corresponding to the polymerase being in an open state.

3. The method of claim 1, wherein duration of the open period is distinct for each dNTP monomer such that it identifies whether a particular dNTP monomer has been incorporated into the template polynucleotide.

4. The method of claim 1, wherein the solution comprises four dNTP monomers, and wherein a first dNTP is present in the solution at a concentration such that the duration of its open period minimally overlaps with the duration of the open period of a second dNTP; wherein the second dNTP is present in the solution at a concentration such that the duration of its open period minimally overlaps with the duration of the open period of the first dNTP and a third dNTP; wherein the third dNTP is present in the solution at a concentration such that the duration of its open period minimally overlaps with the duration of the open period of the second dNTP and a fourth dNTP; and wherein the fourth dNTP is present in the solution at a concentration such that the duration of its open period minimally overlaps with the duration of the open period of the third dNTP.

5. The method of claim 1, wherein the duration of open periods for each dNTP are determined based on a distribution of a plurality of open duration periods.

6. The method of claim 1, wherein the first dNTP is present at a saturating concentration.

7. The method of claim 4, wherein extent of overlap is 1% or less.

8. The method of claim 1, wherein the bioelectronic signature comprises a closed period corresponding to the polymerase being in a closed state.

9. The method of claim 8, wherein at least one characteristic of the closed period varies based on the previously incorporated nucleotide.

10. The method of claim 8, wherein the at least one characteristic of the closed period is identified using a method comprising machine learning.

11. The method of claim 10, wherein the machine learning method comprises Hidden-Markov Modeling or Bayesean non-parametric analysis.

12. The method of claim 1, wherein a combination of at least one characteristic of the closed period and at least one characteristic of the open period is used to identify each of the complementary dNTPs incorporated into to the template polynucleotide.

13. The method of claim 1, wherein the polynucleotide template is DNA.

14. The method of claim 1, wherein the exonuclease activity of the polymerase is disabled.

15. The method of claim 1, wherein the polymerase is functionally coupled to the first and second electrodes using a linker comprising thio-streptavidin.

16. The method of claim 15, wherein linker is attached to a region of the polymerase that is inactive.

17. The method of claim 1, wherein the method comprises applying a voltage bias between the first and second electrodes that is 100 mV or less.

18. The method of claim 1, wherein the dNTP monomers comprise adenine (dATP), cytosine (dCTP), guanine (dGTP), and thymine (dTTP).

19. A method of calibrating a bioelectronic device, the method comprising:
   (a) introducing a template polynucleotide to the bioelectronic device, wherein the bioelectronic device comprises a polymerase functionally coupled to at least a first electrode and a second electrode;
   (b) introducing a solution comprising dNTP monomers to the device comprising the template polynucleotide, each dNTP present in the solution at a saturating concentration;
   (c) obtaining a bioelectronic signature of polymerase activity based on current fluctuations as each complementary dNTP monomer is incorporated into the template polynucleotide, wherein the bioelectronic signature comprises an open period corresponding to the polymerase being in an open state; and
   (d) measuring or determining the intrinsic distribution of the open periods for each dNTP, wherein the bioelectronic device is calibrated based on the distribution of open periods.

20. The method of claim 19, wherein the bioelectronic signature comprises a closed period corresponding to the polymerase being in a closed state, and wherein the bioelectronic device is calibrated based on at least one characteristic of the closed period.

* * * * *